United States Patent
Lang et al.

[11] Patent Number: 5,851,636
[45] Date of Patent: Dec. 22, 1998

[54] CERAMIC PACKING WITH CHANNELS FOR THERMAL AND CATALYTIC BEDS

[75] Inventors: Ko C. Lang, Agoura Hills, Calif.; Jun Huang, Xigu, Lanzhou, China

[73] Assignee: Lantec Products, Inc., Agoura Hills, Calif.

[21] Appl. No.: 630,958

[22] Filed: Apr. 5, 1996

Related U.S. Application Data

[60] Provisional application No. 60/009,876, Dec. 29, 1995.
[51] Int. Cl.⁶ .............................. B32B 3/28; B32B 31/00; F28F 3/00
[52] U.S. Cl. .......................... 428/167; 428/99; 428/120; 428/166; 428/172; 428/192; 156/89.22; 156/290; 156/292; 165/166; 261/DIG. 72
[58] Field of Search ................................... 428/137, 120, 428/167, 172, 192, 166, 99; 156/60, 290, 292, 302.4, 89.22; 165/9.1, 166, 167, 1.8, DIG. 72

[56] References Cited

U.S. PATENT DOCUMENTS

| | | |
|---|---|---|
| 4,521,532 | 6/1985 | Cho .......................................... 428/116 |
| 4,567,086 | 1/1986 | Fukuda et al. ............................ 428/166 |
| 4,624,305 | 11/1986 | Rojey ....................................... 165/166 |
| 4,705,797 | 11/1987 | Mita ............................................ 165/4 |
| 4,771,826 | 9/1988 | Grehier ................................... 165/166 |
| 4,776,387 | 10/1988 | Newman .................................. 165/76 |
| 4,901,787 | 2/1990 | Zornes ........................................ 165/4 |
| 5,025,856 | 6/1991 | Van Dyke ............................... 165/167 |

*Primary Examiner*—Donald Loney
*Attorney, Agent, or Firm*—Marvin E. Jacobs

[57] ABSTRACT

A ceramic packing element is formed from a stack of ceramic plates having parallel ribs forming parallel grooves therebetween. The grooves are closed into channels by the surface of an opposed plate. The ribs may engage the end surfaces of ribs on an adjacent space or may be interleaved with the ribs of an opposed plate to form smaller channels. The plates are adhered to each other by firing a stack of plates in the green state or wrapping film or bands around a stack of pre-fired plates. The elements may be preassembled into larger units before placement in a column by wrapping metal bands around an assembly of elements.

22 Claims, 6 Drawing Sheets

CERAMIC PACKING WITH CHANNELS FOR THERMAL AND CATALYTIC BEDS

CROSS-REFERENCE TO RELATED APPLICATION

This application is a complete application and a continuation-in-part of provisional application Ser. No. 60/009,876 filed Dec. 29, 1995.

TECHNICAL FIELD

The present invention relates to processes utilizing beds of ceramic packing to heat and/or react a body of fluid or act as a carrier for a catalyst and, more particularly, this invention relates to such processes utilizing improved ceramic packings for the beds.

BACKGROUND OF THE INVENTION

Regenerative thermal beds are used to capture and store heat from a first hot stream of fluid and then to transfer the heat to a second cold body of fluid before it is reacted such as by combustion, oxidation, reduction or other chemical process whether reacted in the presence or absence of a catalyst.

Originally gravel was used as the packing for the bed. Ceramic saddles and Raschig rings have been utilized for decades. As the saddles and Raschig rings randomly pack into the heat exchanger shell, they may locally stack in an orientation that will block flow. The flow is non-uniform throughout the bed of material and the pressure drop through a heat exchanger containing saddles, gravel or rings is relatively high, usually about 10 inches of water. Furthermore, the locally blocked areas may trap fluid which can contaminate the flow of second fluid or can be exhausted to the environment.

Recently, the use of monolithic columns of ceramic material for the heat exchanger columns in a regenerative thermal oxidizer system for cleaning combustion gas has been disclosed in U.S. Pat. No. 5,352,115. The monolithic columns have a lower pressure drop and reduce contamination experienced with random packing of saddles or rings.

Monolithic columns carrying a layer of catalyst are also used in catalytic processes to synthesize or convert gaseous streams to other products and in the treatment of exhaust gases from combustion engines or from industrial processes. The ceramic columns are coated with catalyst materials, such as rare earth metals. However, it is expensive to manufacture monolithic columns. Furthermore, monolithic columns are rigid and brittle. After repeated cycles of heating and cooling, stress cracks develop and the column can develop cracks and break or shatter into small pieces. The column becomes inoperative requiring replacement of the monolithic elements. This can be quite expensive in the case of columns coated with noble or rare earth metals or metallic compounds containing platinum or palladium, rhodium, etc.

STATEMENT OF THE INVENTION

A column having similar architecture to a monolithic column is provided by the invention at a fraction of the cost of manufacturing a monolithic column. Instead of manufacturing the column as a homogenous, unitary body, the column is formed by stacking a plurality of ceramic plates. The plates may be cured or in the green, uncured state. The plates have grooves formed between ribs. When the plates are stacked with the ribs and grooves parallel to the ribs and grooves on an opposing plate, an element is formed having a plurality of channels extending through the element.

The ribs on the plate can be adhered to the opposed surface. If the surface is planar, the opposing surface closes the channel. The volume and cross-section of the channel will be defined by the volume and cross-section of the groove. The plates can have one flat side and one grooved side. The plates can be flat and have a regular or irregular polygonal shapes such as a square, rectangular, triangular, pentagonal, hexagonal or circular. The plates can have a regular undulating cross-section or a repeating polygonal cross-section. The plates can be the same size or can increase in size and/or decrease in size in the stack. The plates can be curved into a closed cylinder and each plate will have a diameter larger than the preceding plate by the thickness of the preceding plate. All the grooves are preferably parallel to each other so that the plates can be stacked with the columns in alignment. The grooves can all be parallel to a set of opposed side walls or the grooves can be at an angle such as 30° to 60° to a set of opposed end walls.

The size of the plates and of the elements formed from the plates depend on the intended utility of the elements. If the elements are to be used in a catalytic automotive reactor, the elements are stacked end to end and side by side to form a column. The elements are usually rectangular and are formed of square plates. The plates can be from 0.5 inch to 12 inches usually 1 to 4 inches in height and width. The thickness of the plates can be from 0.01 to 1.0 inches, usually 0.04 to 0.1 inch. The height of the elements can be from 0.5 inches to 50 inches, usually from 1 inch to 12 inches.

If the elements are to be used as random packing in a tower, the elements are preferably polygonal in shape and usually have a diameter from 0.2 to 5 inches, generally from 0.5 to 3 inches. The grooves can be curved, triangular or rectangular in cross section. The top of the ribs can be pointed, flat or rounded. A flat top is preferred since the contact surface for bonding or closing a channel will be larger. The grooves are preferably as small as possible and as closely spaced as possible. Usually the grooves will be from 0.01 inch to 1.0 inches in depth and width, preferably from 0.04 to 0.5 inches.

Another configuration for the element is one in which instead of the end of a rib being secured to the end face of an opposed rib or planar surface, one or more ribs can be disposed in a single groove in the opposed surface. The end of the rib(s) extends to the bottom surface of the groove, dividing the groove into 2 or more mini-channels. This provides an easy and reliable method to decrease the size of the channels without the need to cast or extrude plates with very small grooves.

The elements of the invention contain about the same amount of ceramic material as an equivalently sized monolithic element. However, manufacturing costs are considerably less. The ribbed plate can be produced by stamping, casting or extrusion. The plates are cut into the desired shape and stacked in the green or fired state into the shape of an element. The elements formed from green, uncured plates are manufactured by firing the stack of green plates.

When the stacks are fired, the portions of the ribs in contact with the opposed ribs or wall fuse together. However, the many points that the ribs do not adhere act as stress relievers that accommodate the expansion and contraction of the plates and prevent the ribs or plates from cracking. This may form cracks between the channels. However, since the process gases are flowing in the same direction there is no loss of efficiency.

Elements can also be formed by first firing the plates. The cured plates are then stacked into an element and stabilized by adhering the pre-fired elements with adhesive or by binding the stack with bands or wrappers. The bands or wrappers can be metal or a fugitive material such as an organic plastic such as polyethylene or Saran wrap. The fugitive organic materials are vaporized during initial heating of the heat exchanger or column of elements. Stacking of the elements into an ordered column can be facilitated by binding a plurality of the elements into a multi-element structure by aligning elements side by side and top to bottom in a stack and binding the stack together by adhesive or by mechanical binding means such as wire, wire mesh, metal clips or metal bands.

The ceramic plates and elements are generally formed from refractory clays generally containing such constituents as $S:O_2$, $Al_2O_3$, Mgo, CaO, $K_2O_2$, etc. The ceramic element is inert to the gases passing through the regenerative heat exchanger and remains solid at the highest temperature achieved during the process.

A test was conducted comparing a column formed from elements formed of ribbed plates according to the invention stacked with their channels aligned to a monolithic column having the same surface area. Surprisingly, the yield was 20% higher when using the stacked elements of the invention. It was expected that the yield would be lower since the irregular surfaces of the channels formed from the cast elements would increase flow resistance and decrease yield. Perhaps the rough surfaces of the channels perturbs or disturbs the boundary layer next to the surfaces and increases mixing and reaction between the gases flowing in the boundary layer.

Even though the elements formed by firing green plates after assembly into an element provides stress relief at points where the plates do not adhere it is found that elements formed from pre-fired plates perform as well and result in even less stress cracking. Furthermore, it is much cheaper to first fire the plates and assemble them later. Also the rigid fired plates are easier to handle than the soft green plates. Also the fixed in place, and rigid ribs in a fired plate can be pressed together without deforming the ribs or plate. The soft moldable ribs in a green plate can bend and stretch when handled or placed under force.

These and many other features and attendant advantages of the invention will become apparent as the invention becomes better understood by reference to the following detailed description when considered in conjunction with the accompanying drawings.

DETAILED DESCRIPTION OF THE INVENTION

Figure 1:
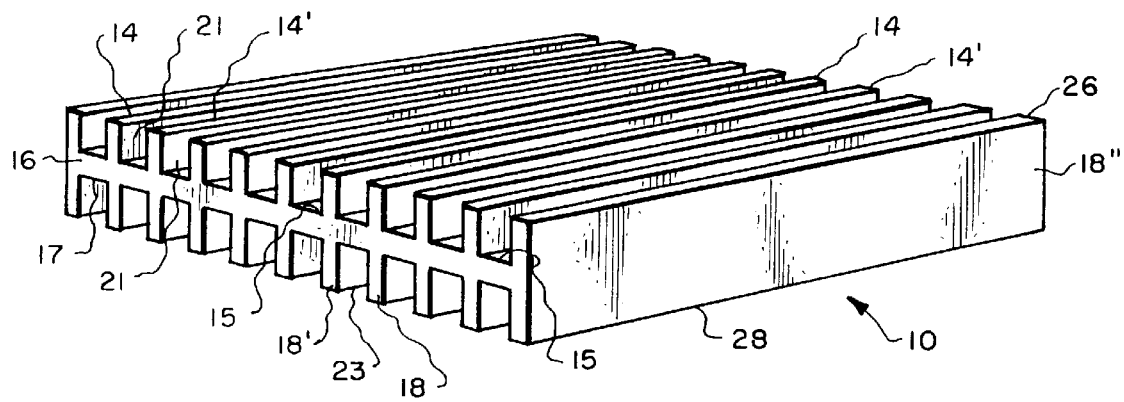
FIG. 1 is a perspective view of a first embodiment of a ribbed plate according to the invention.
Figure 2:
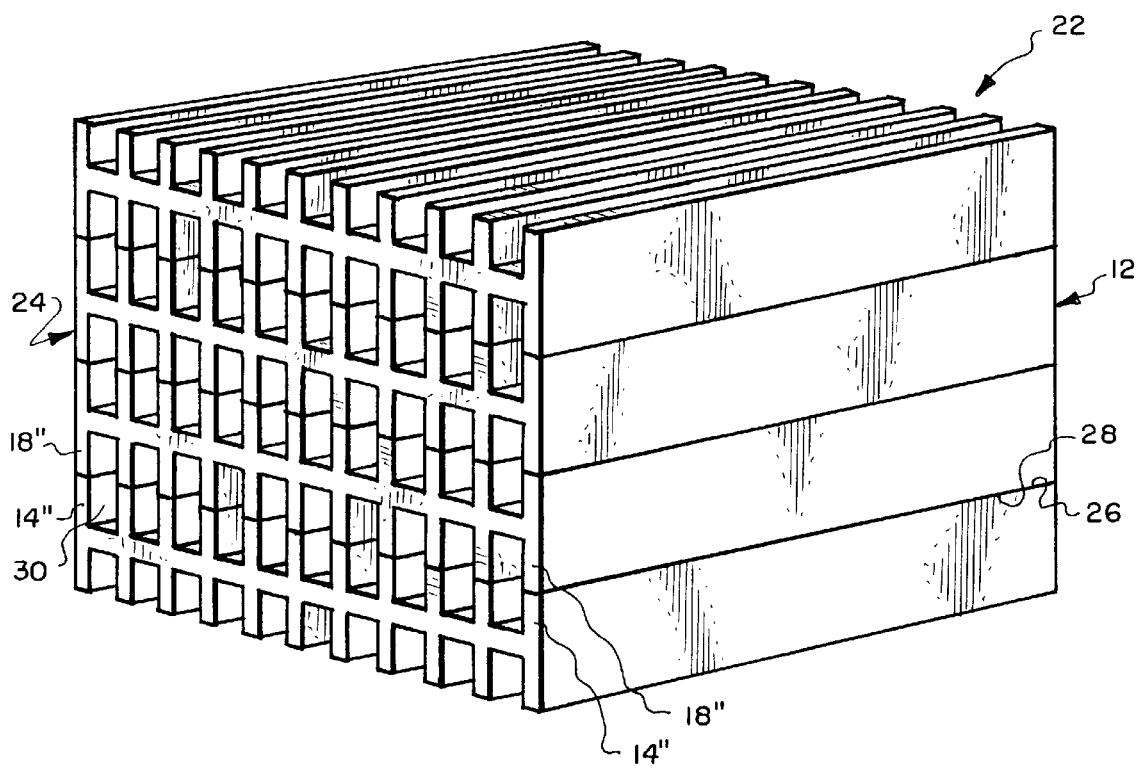
FIG. 2 is a perspective view of an element formed from a cured stack of a plurality of the ribbed plates shown in FIG. 1.

Referring now to FIGS. 1 and 2, a plate 10 is shown which can be in the green state or fired to the cured state. Cured plates can be stacked and adhered together by adhesive or by mechanically holding the stacked plates together such as by plastic wrappers or ties, bands, metal clips, etc. Plates 10 in the green or fired state can be stacked to form an element 12 as shown in FIG. 2.

Plate 10 contains a plurality of parallel ribs 14 extending from the top surface 15 of central member 16 and a plurality of parallel ribs 18 extending from the bottom surface 17 of the central member 16. Grooves 21, 23 are formed between adjacent ribs 14, 14' and 18, 18'. The opposed end faces 26, 28 of end ribs 14" and 18" join to form end walls 22, 24. The end faces 26, 28 of opposed and adjacent intermediate ribs 14, 18 join to form closed channels 30 having the combined volume of grooves 21 and 23. As previously discussed, instead of stacking the plates 10 such that the opposed ends 26, 28 of ribs 14, 18 are adjacent, the plates can be stacked with the ribs 14, 18 entering the opposed grooves 21, 23 to form two channels out of each groove.

Figure 3:
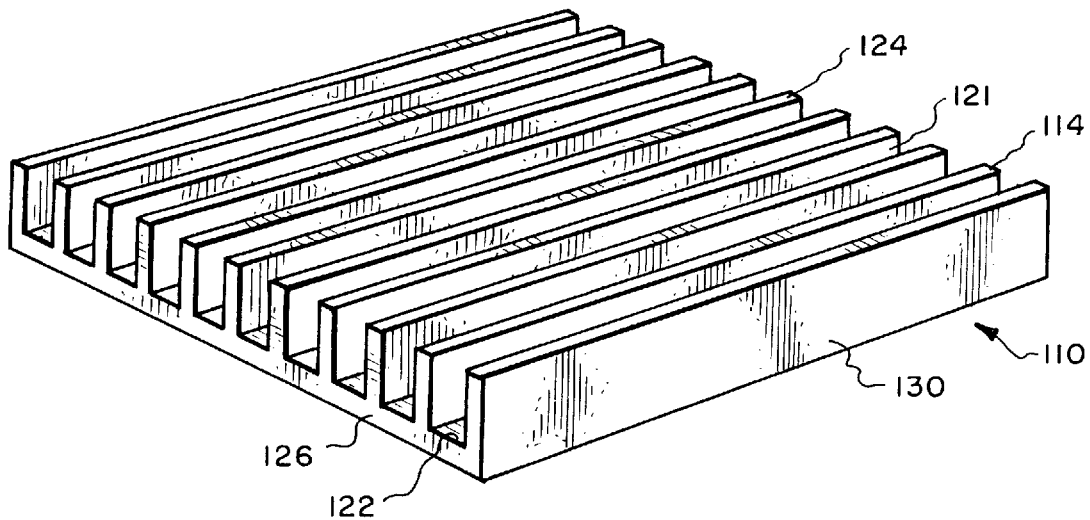
FIG. 3 is a perspective view of another embodiment of a ribbed plate according to the invention.
Figure 4:
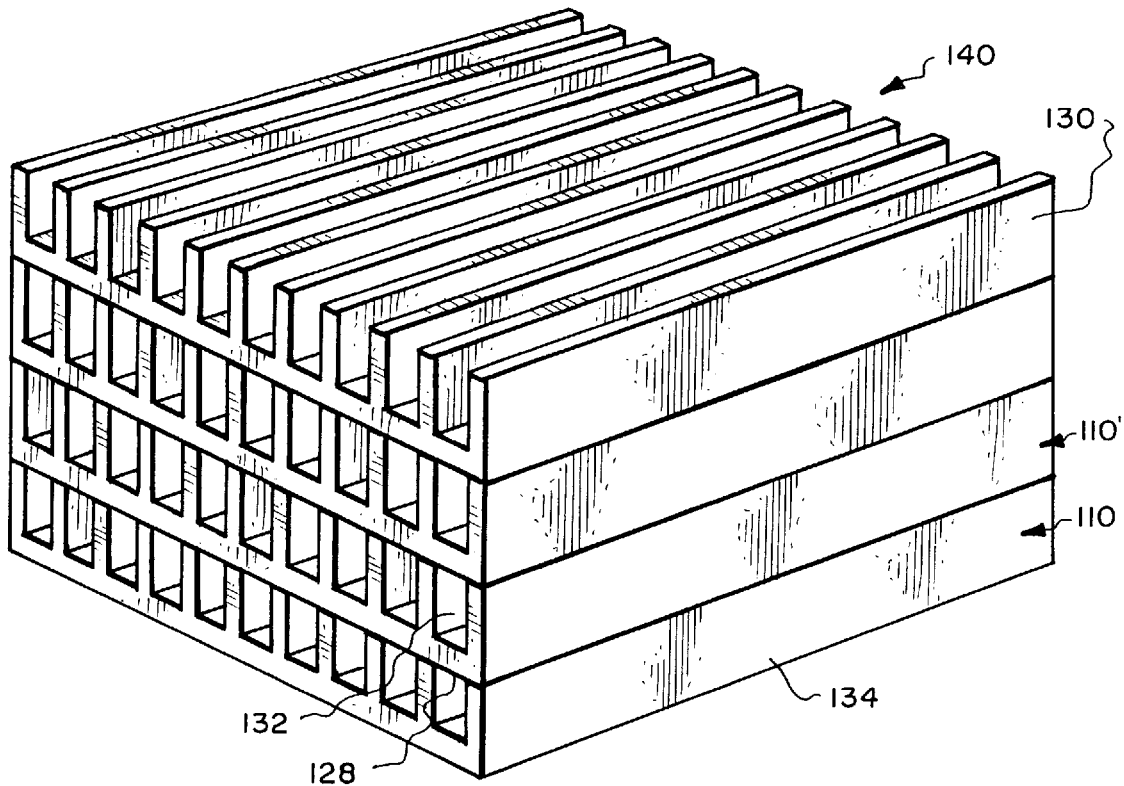
FIG. 4 is a perspective view of an element formed from a cured stack of the ribbed plates shown in FIG. 3.

Referring now to FIGS. 3 and 4, in a second embodiment of the invention, the plate 110 contains ribs 114 and grooves 121 extending from the top surface 122 of the support member 126 of the plate 110. The plates 110 are shown stacked with the end faces 124 of the ribs 114 attached to the rear face 128 of the opposed plate 110' to form an element 140. The rear face 128 closes the grooves 121 between ribs to form channels 132. The end ribs 130 join together to form a closed end wall 134.

Some of the plates 114 could also be stacked with the opposed ribs facing and joined to each other to form larger channels, not shown, or some of the plates could be stacked with the ribs entering the grooves and adhered to the bottom of the grooves to form smaller channels.

Figure 5:
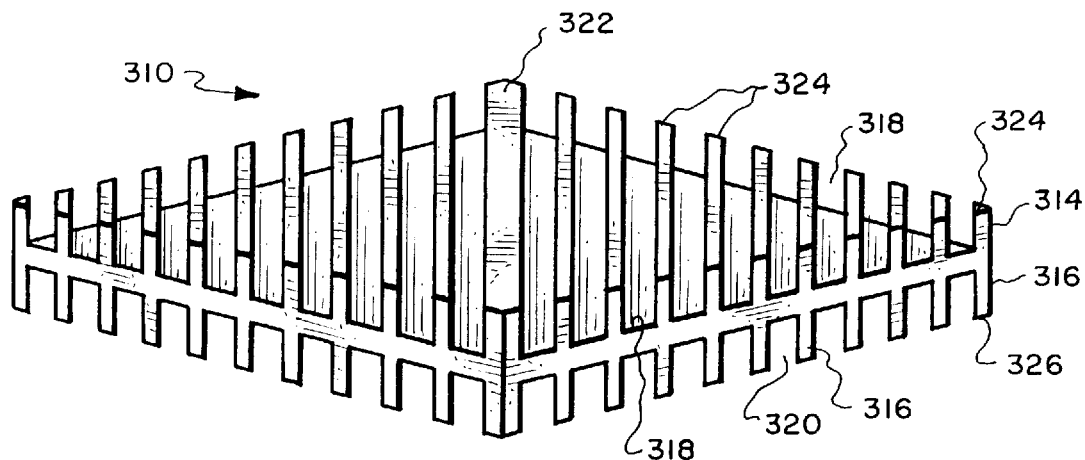
FIG. 5 is a perspective view of a further embodiment of a ribbed plate.
Figure 6:
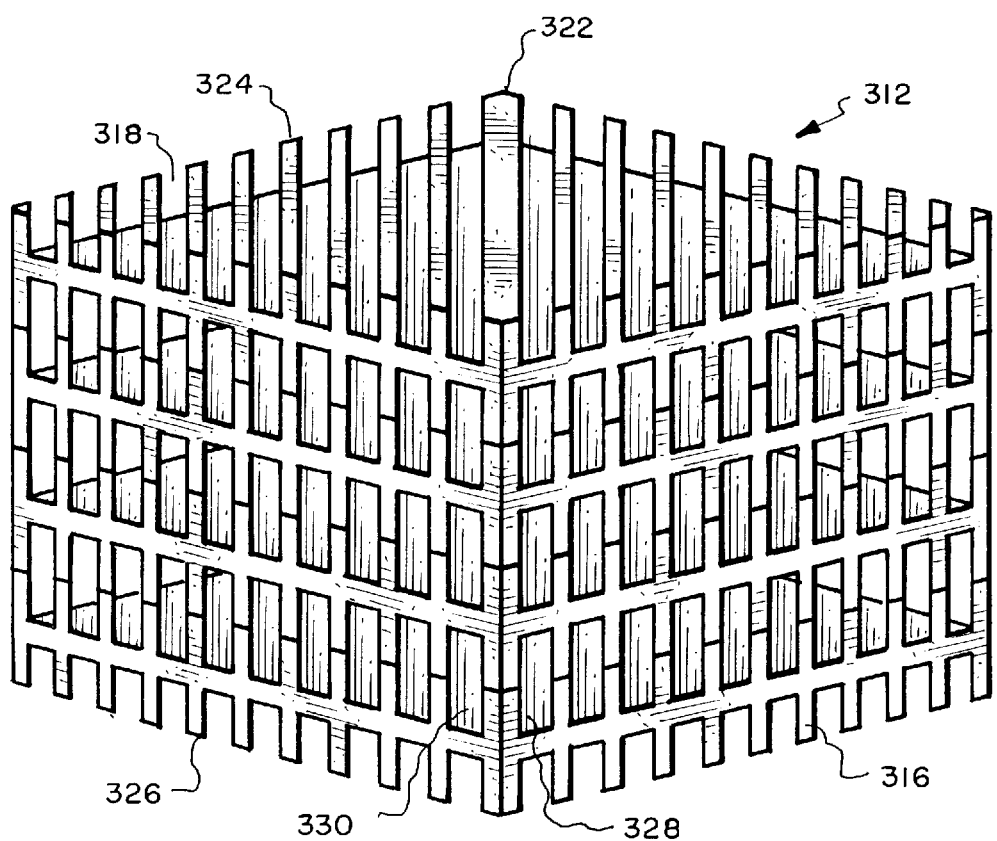
FIG. 6 is a perspective view of a cured stack of plates shown in FIG. 5 in the form of an element.

Referring now to FIG. 5 and 6, a third embodiment of a plate 310 and element 312 is illustrated. The ribs 314, 316 and grooves 318, 320 are formed parallel to a central diagonal rib 322. The end faces 324, 326 of the ribs 314, 316 in element 312 are shown in engagement forming channels 328, 330. The ribs could also be interleaved with the grooves to form smaller channels as shown in FIG. 7.

Figure 7:
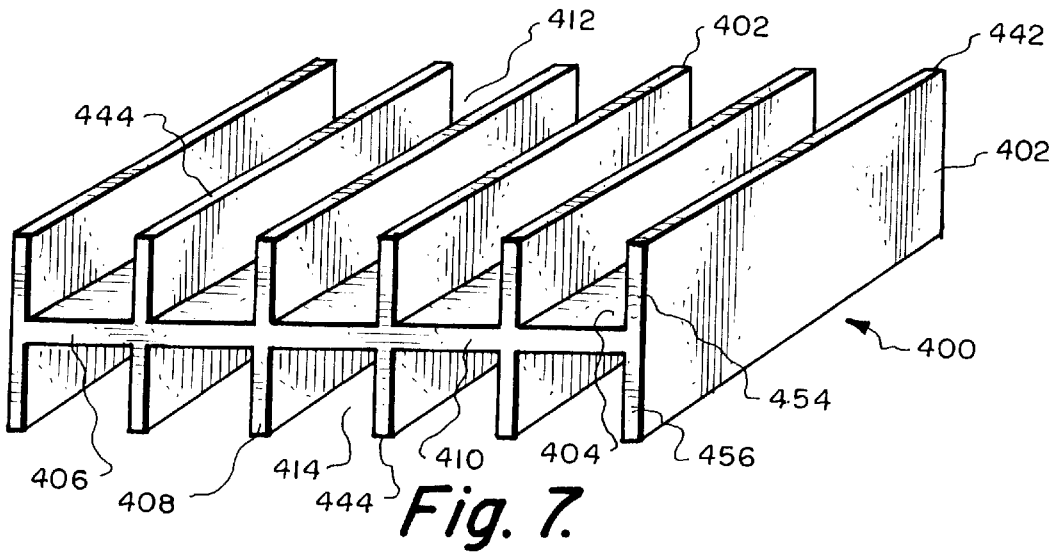
FIG. 7 is a perspective view of still another embodiment of a ribbed plate.

The plate 400 shown in FIG. 7 contains a plurality of parallel ribs 402 extending from the top surface 404 of the central member 406 and a plurality of parallel ribs 408 extending from the bottom surface of 410 of the central member 406. In order to form a planar side wall 430, an opposed plate 424 contains one less rib 418', 420' on each side of the central member 428 than the plate 400. The first rib 421, 422 of the plate 424, on each side of the central member 428 is indented ½ groove 432 from the side edge 436. The ribs 402, 408 are narrower than the grooves 412, 414 on the plate 400 and the ribs 418, 420 on the plate 424 are narrower than the grooves 437, 438, preferably occupying no more than ⅓ the distance between adjacent ribs 402, 408 or 418, 420.

Figure 8:
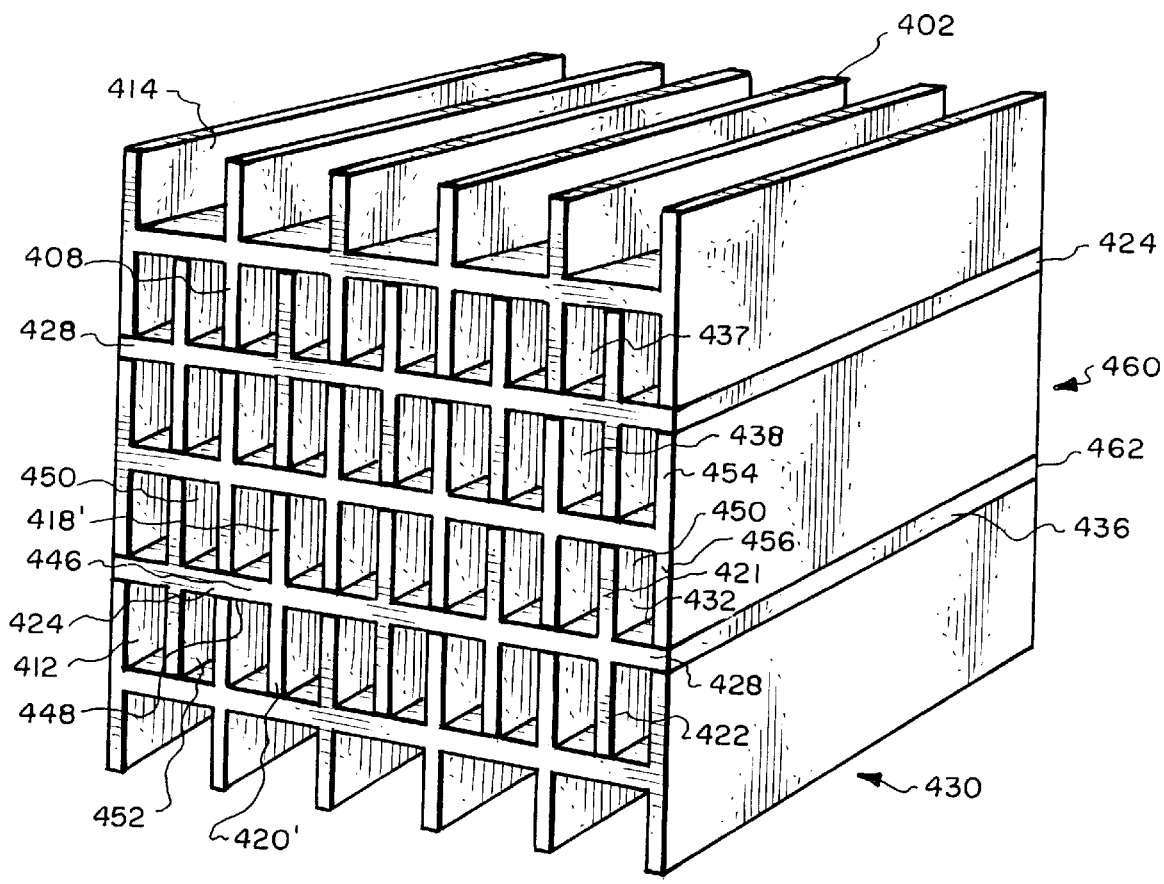
FIG. 8 is a perspective view of a cured stack of plates with the ribs of one plate as shown in FIG. 7 disposed in the grooves in an opposed plate dividing the groove into smaller channels.

As shown in FIG. 8, an element 460 is assembled by disposing the ribs 402, 408 into the grooves 437, 438 of an opposed plate 424 with the end faces 442, 444 of the ribs 402, 408 seated on the bottom surfaces 446, 448 of the opposed grooves 437, 438. The ribs 402, 408 divide each groove 437, 438 into 2 channels 450, 452. The end ribs 454, 456 close the open ends of the plates 424 to form the end small channel 462. An assembly of uncured plates is fired to form an element 460. The plates 400 and 424 can be pre-fired, assembled into a stack 460 and joined into an element by adhesive or by mechanical holding measures as previously disclosed.

The plates 400, 424 need not have ribs extending from each surface. The back surfaces can be planar. The back surfaces can be adhered to end surfaces of ribs or to the back of another plate. The grooves may accept more than one rib such as 1 to 4 ribs. The element may contain all plates interleaved to form smaller channels or some plates may have regions of interleaved ribs and grooves and other regions where the ends of the ribs are attached to the ends of the opposing ribs. Some plates may contain long ribs which enter grooves and some short ribs which abut ribs on the opposed plate.

Figure 9:
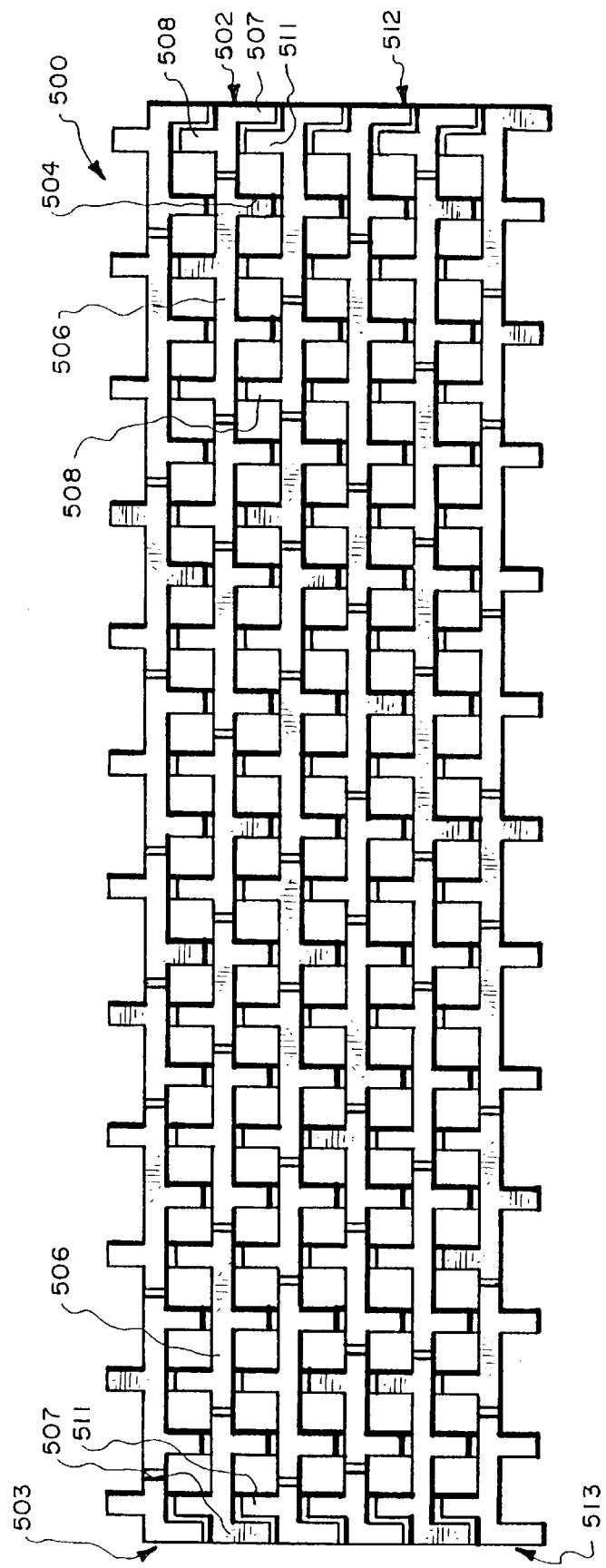
FIG. 9 is a front view in elevation of a stack of cured plates joined by a fugitive wrap.
Figure 10:
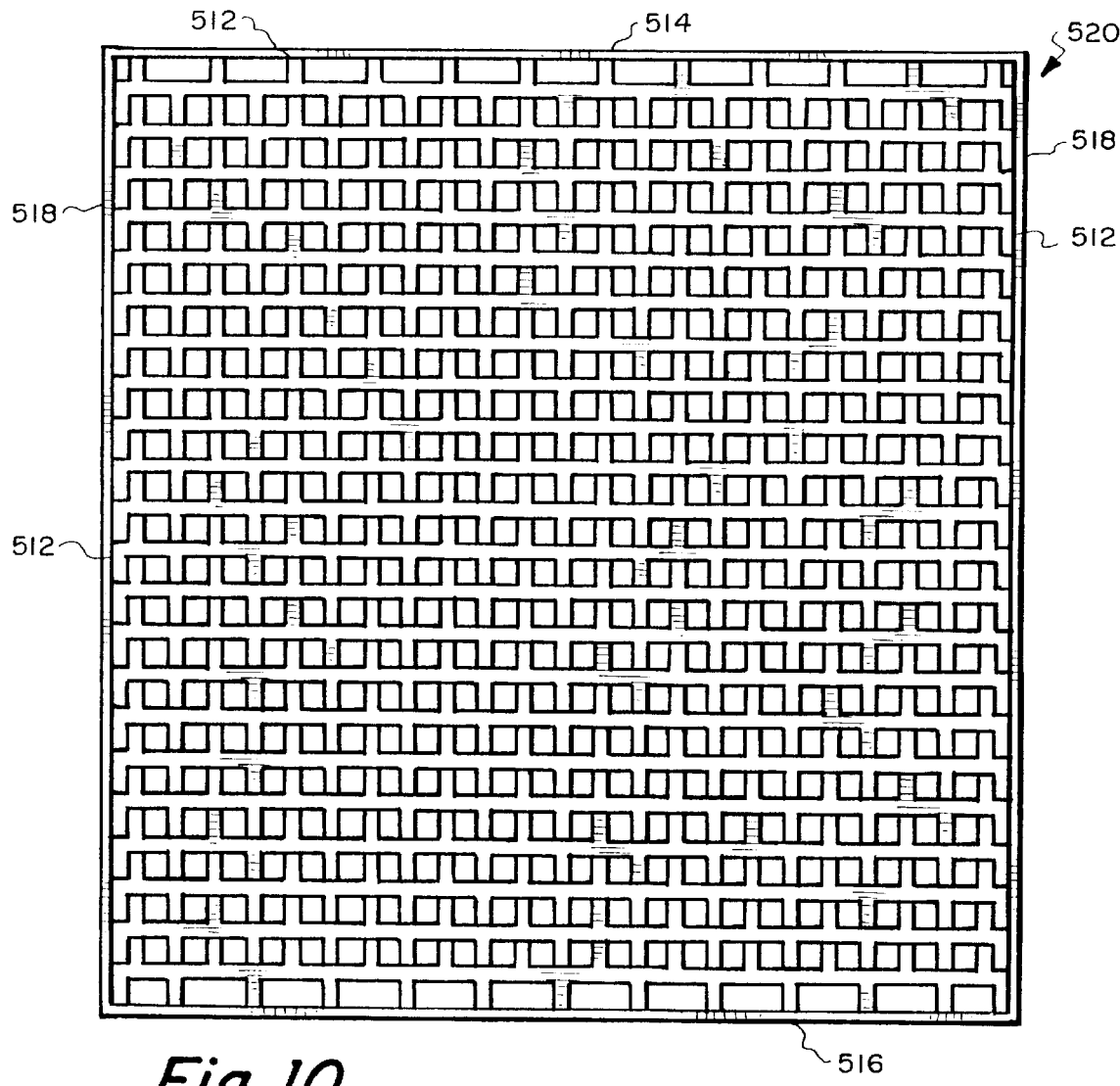
FIG. 10 is a front view in elevation of a stack of fired plates.

Elements in which the plates are adhered to each other, form a brittle ceramic body. Even though there is some freedom of movement where a rib does not adhere to the end of an opposed rib or to the inner surface of the central support, the element can still crack and crumble and degrade when repeatedly heated and cooled during regenerative thermal processing. The element 500 shown in FIGS. 9–10 is formed of interleaved plates 502, that are not adhered to each other by heat curing or by adhesive.

The plate 502 has a plurality of parallel ribs 504 extending downward from the central support 506. The end ribs 507 start and end coincident with the end of the central member. The ribs 508 extend upwardly from the central support 506. The end ribs 511 are indented from the edges 513 of the central support by about the width of an end rib 507. When the plates 502, 503 are stacked, the end ribs 507 are locked into the indented spaces which prevents the unadhered plates from sliding. The end ribs 507 in combination with the central supports 506 form end walls 512.

It would be time consuming to place each plate into a column. Furthermore, breakage can occur during handling of the individual plates or stacks of plates while they are filled into the shell of a RTO or catalytic column or a heat exchanger. As shown in FIG. 10, a stack of plates can be held together by wrapping the plates along the end walls 512 and across the top surface 514 and bottom surface 516 with a wrap 518 of strong plastic, preferably a shrink wrap such as Saran which is a vinyl acetate-vinylidene chloride copolymer. The element 520 can then be handled as a stable entity and placed in the column or on top of and/or adjacent similar stacked elements. When hot gases first enter the column, the wrapper will decompose into gaseous products and will be exhausted from the column by the hot gases.

Figure 11:
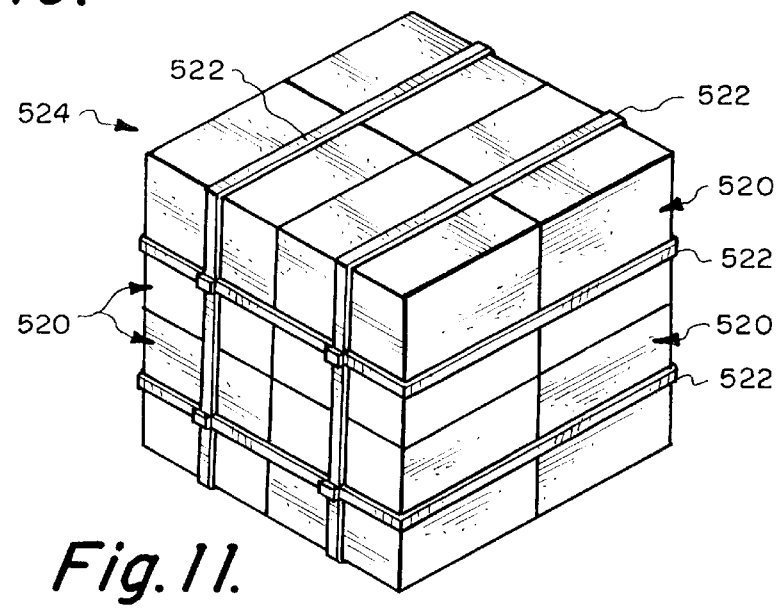
FIG. 11 is a perspective view of an assembly of elements adhered by metal bands.

In order to further speed filling of a column, not shown, a plurality of elements 520 can be joined together by metal straps 522 to form an assembly 524 as shown in FIG. 11.

The elements and modules can be assembled into assemblies of varying sizes and shapes. Preferably, the assembly has a rectangular column configuration or a cube configuration. The modules can be aligned with the side by side modules having channels parallel to each other and the end to end modules having the channels in the same axial alignment. Eight 6 inch cubical modules will form a 1 foot square cube assembly. Eighteen 4 inch cubical modules will also form a 1 foot cubical assembly.

It is to be realized that only preferred embodiments of the invention have been described and that numerous substitutions, modifications and alterations are permissible without departing from the spirit and scope of the invention as defined in the following claims.

We claim:

1. A ceramic plate packing element comprising a first plate and an opposed plate, each having a first end and a second end and a first surface and a second surface, at least said first surface of said plate first and opposed plates, each containing a plurality of parallel, continuous ribs having a first end surface extending from the first surface of the plate forming parallel grooves between the ribs, the distance between grooves being greater than the width of an opposed rib and the length of the ribs being substantially equivalent to the depth of the grooves, the grooves terminating in a bottom surface, being interleaved with the ribs on said first plate being interleaved with the ribs on the opposed plate, the continuous end surface of said ribs being in contact with the bottom surface of the grooves, said bottom surfaces substantially closes said grooves to form channels.

2. A ceramic packing element according to claim 1 in which at least one of the plates is planar.

3. A ceramic packing element according to claim 1 in which the second surface of at least one of the plate also contains parallel ribs and grooves.

4. A ceramic packing element according to claim 1 in which the spacing between adjacent ribs is larger than the width of the ribs.

5. A ceramic packing element according to claim 1 in which the ceramic is in a green state.

6. A ceramic packing element according to claim 1 in which the ceramic is in a cured state.

7. A ceramic packing element according to claim 6 in which the surfaces contain a catalytic layer.

8. A ceramic packing element according to claim 1 in which the plates have a width and depth from 0.5 to 12 inches and a thickness from 0.01 to 1.0 inches.

9. A ceramic packing element comprising:

a stack of individual, ceramic plates a first plate having a first surface including a plurality of parallel, continuous ribs forming a plurality of parallel grooves between the ribs, said ribs each having an inner end connected to the first surface and a continuous outer end surface and said grooves having a continuous bottom surface;

a second ceramic plate having parallel, continuous ribs forming parallel grooves therebetween, said grooves being wider than opposed ribs and having a bottom surface in close contact with the outer end surfaces of said ribs to form parallel substantially closed channels between said ribs; and means for adhering said plates together to form said element.

10. A ceramic packing element according to claim 9 in which the ceramic adhering means comprises curing plates in the green state whereby said surfaces in contact from an adhering bond.

11. A ceramic packing element according to clam 9 in which said adhering means comprises mechanical means for holding said surfaces in contact.

12. A ceramic packing element according to claim 11 in which the mechanical means comprises a length of plastic film wrapped around said element in a direction parallel to said channels.

13. A ceramic element according to claim 9 in which the adhering means comprises adhesive.

14. A ceramic packing element according to claim 9 in which the spacing between ribs is wider than the width of the ribs and the ribs on opposed surfaces are interleaved.

15. A ceramic packing element according to claim 9 in which the ribs on the first surface of the second plate are spaced further apart than the ribs on the first surface of the first plate and at least some of said ribs interleave and seat on the bottom surface of the opposed grooves.

16. A ceramic packing assembly comprising a plurality of packing elements as defined in claim 9 placed into an assembly with their channels in alignment and means securing the elements together.

17. An assembly according to claim 16 in which the securing means comprises metal bands.

18. A method of forming a ceramic packing element comprising the steps of:

forming on a first surface of a plurality of ceramic plates a plurality of parallel, continuous ribs having continuous, outer end surfaces and parallel grooves therebetween having bottom surfaces, stacking the plates such that the ribs on opposed plates are interleaved with the continuous outer end surfaces of the ribs contacting the opposed bottom surfaces of the grooves to form channels; and adhering said outer end surfaces of the ribs to said opposed bottom surfaces.

19. A method according to claim 18 in which the ceramic of said first and second elements is in the green state and said surfaces are adhered by curing said ceramic to form a bond between said surfaces.

20. A method according to claim 18 in which the ceramic elements are in the cured state and in which the plates are adhered by placing a wrapping around the elements in a direction parallel to the channels.

21. A ceramic packing element formed of a stack of plates having ribs and grooves on the surfaces of the plates including means for latching a plate to an adjacent opposed plate which cooperates with end ribs of the plates to prevent movement of the plates in a direction normal to the ribs and grooves.

22. A ceramic packing element according to claim 21 in which said end ribs on a first plate are disposed at the side of the plate and the end ribs of an opposed plate are indented by the thickness of said end ribs on the first plate whereby when the plates are assembled with the end ribs of the first plate adjacent the indented end ribs of the opposed plate, movement perpendicular to the channels is prevented.

* * * * *